US00PP15052P3

(12) United States Plant Patent
Meilland

(10) Patent No.: US PP15,052 P2
(45) Date of Patent: Jul. 27, 2004

(54) CLIMBING ROSE PLANT NAMED 'MEIDRASON'

(50) Latin Name: *Rosa hybrida*
Varietal Denomination: cv. Meidrason

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 10/114,987

(22) Filed: Apr. 4, 2002

(65) Prior Publication Data

US 2002/0170097 P1 Nov. 14, 2002

(30) Foreign Application Priority Data

Apr. 4, 2001 (FR) ..... PBR 17668

(51) Int. Cl.[7] ..... A01H 5/00
(52) U.S. Cl. ..... Plt./115
(58) Field of Search ..... Plt./115

*Primary Examiner*—Anne Marie Grunberg
*Assistant Examiner*—Annette H Para
(74) *Attorney, Agent, or Firm*—Burns, Doane, Swecker & Mathis, L.L.P.

(57) ABSTRACT

A new and distinct variety of Climbing rose plant is provided which abundantly forms very double dark red blossoms having a strong fragrance that are of the old rose type. The stability of the flower coloration is good. The plant displays good vigor and exceptional resistance to diseases. The foliage is very dense, medium green and semi-glossy, and contrasts nicely with the blossom coloration. The new variety is particularly well suited for growing as attractive ornamentation in the landscape where a climbing rose plant is desired.

1 Drawing Sheet

Botanical/commercial classification: *Rosa hybrida*/ Climbing Rose.

Varietal denomination: cv. 'Meidrason'.

SUMMARY OF THE INVENTION

The new variety of *Rosa hybrida* Climbing rose plant was created by artificial pollination wherein two parents were crossed which previously had been studied in the hope that they would contribute the desired characteristics. The female parent (i.e., the seed parent) was the product of the 'Delsap' variety (non-patented in the United States). The male parent (i.e., the pollen parent) was the 'Kortello' variety (non-patented in the United States). The parentage of the new variety can be summarized as follows:

'Delsap'×'Kortello'.

The seeds resulting from the above pollination were sown and small plants were obtained which were physically and biologically different from each other. Selective study resulted in the identification of a single plant of the new variety.

It was found that the new rose variety of the present invention:

(a) exhibits a climbing growth habit, (b) abundantly forms attractive very double dark red blossoms having a strong fragrance that are of the old rose type, (c) forms very dense medium green semi-glossy foliage that contrasts well with the blossom coloration, (d) displays good vigor, (e) displays exceptional disease resistance, and (f) is particularly well suited for growing as attractive ornamentation in the landscape.

The stability of the flower coloration is good.

The new variety well meets the needs of the horticultural industry and can be used to advantage for growing in the landscape where an attractive climbing rose plant is desired.

The new variety of the present invention can be readily distinguished from its ancestors. For instance, the 'Delsap' variety displays an upright growth habit and brighter color, and 'Kortello' variety displays a shrub growth habit and forms blossoms having only approximately 35 petals.

When compared to the 'Blaze' variety (U.S. Plant Pat. No. 10), the new variety of the present invention forms larger and more vivid red blooms.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meidrason' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during June while budded on *Rosa laxa* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of one year-old plants during June while budded on *Rosa laxa* understock and growing outdoors at Le Cannet des Maures, Var, France.

Class: Climbing.

Plant:

*Height.*—Approximately 170 to 200 cm on average at the end of the growing season.

*Width.*—Approximately 100 to 120 cm on average at the end of the growing season.

*Habit.*—Climbs well with support.

Branches:

*Color.*—Young stems: near Yellow-Green Group 146C and slightly suffused with Greyed-Red Group 182B. Adult wood: near Yellow-Green Group 146B.

*Thorns.*—Size: variable (as illustrated), with the longest thorns commonly being approximately 10 mm in length. Quantity: a young stem having a length of 10 cm commonly will bear approximately 8 thorns having lengths greater than 5 mm, and an adult stem having a length of 10 cm commonly will bear approximately 9 thorns having lengths greater than 5 mm. Configuration: fairly straight on upper surface and concave on the under surface (as illustrated). Color: on young stems near Yellow-Green Group 146B suffused with Greyed-Red Group 182B, and on adult stems Yellow-Green Group 146D suffused with Greyed-Orange Group 173D.

Leaves:

*Stipules.*—Adnate, pectinate, approximately 1.5 cm in length and approximately 0.2 cm in width, and near Green Group 139B on the upper surface and near Green Group 138B on the under surface.

*Petioles.*—Length: Approximately 2 cm. Upper surface: glandular. Under surface: commonly bear a few prickles. Color: near Green Group 139B on the upper surface and near Green Group 138B on the under surface.

*Leaflets.*—Number: 3, 5, and 7 (most often). Shape: somewhat ovate with a rounded base and a lanceolate tip. Size: terminal leaflets commonly are approximately 5.5 cm in length and approximately 4.5 cm in width. Serration: simple and fairly regular (as illustrated). Texture: smooth and fairly thick. General appearance: very dense, and medium green with a semi-glossy aspect. Color (young foliage): Upper surface: near Yellow-Green Group 146A suffused with Greyed-Red Group 178A. Under surface: near Yellow-Green Group 147A suffused with Greyed-Red Group 178A. Color (adult foliage): Upper surface: near Green Group 139A. Under surface: near Green Group 138A.

Inflorescence:

*Number of flowers.*—Commonly in clusters of 2 to 5 flowers per stem.

*Sepals.*—Five in number, tomentose on the upper surface, smooth on the under surface, elongated, approximately 2.5 cm in length, approximately 1 cm in width, with a pointed apex and a linear base, near Greyed-Green Group 194A in coloration on the upper surface, near Green Group 138A on the under surface, and commonly with small extensions (as illustrated).

*Peduncles.*—Length: approximately 8 cm on average. Texture: bear a few small prickles. Color: near Yellow-Green Group 146A.

*Buds.*—Shape: Ovoid. Size: medium (as illustrated). Length: approximately 2 cm on average. Color: Upper surface: Cardinal Red, Red Group 53A and dull as the calyx breaks. Under surface: Cardinal Red, Red Group 53A and satiny as the calyx breaks.

*Flower.*—Shape: umbrella-shaped when fully open and of the old rose type. Diameter: approximately 10 to 11 cm on average. Margin: external petals are slightly undulated. Color (when blooming): Upper surface: Red Group 46A. Under surface: Red Group 45C. Fragrance: strong. Petal number: approximately 95 to 100 on average under normal growing conditions. Petal arrangement: verticillate. Petal length: approximately 4.5 cm on average. Petal width: approximately 6 cm on average. Petal texture: physically firm. Petaloids: none formed. Petal drop: good with the petals commonly detaching cleanly before drying. Anthers: arranged regularly around the styles, approximately 115 in number on average, approximately 0.3 cm in size, and Yellow-Orange Group 21D in coloration. Filaments: approximately 0.6 cm in length and near Red Group 53C in coloration. Pollen: near Yellow-Orange Group 15A in coloration. Stigma: approximately 0.1 cm in size on average, and near Yellow Group 1D in coloration. Styles: approximately 90 in number on average, approximately 1 cm in length, and near Yellow Group 1D in coloration. Receptacle: funnel-shaped in longitudinal section, approximately 1.2 cm in length, and approximately 1.2 cm in width, and near Yellow-Green Group 146A in coloration. Hips: generally pitcher-shaped, approximately 3 cm in diameter on average, and near Yellow-Green Group 148B widely suffused with Orange-Red Group 31B in coloration. Longevity: a typical blossom commonly lasts approximately 10 to 12 days on average on the plant. The longevity of the blossoms when cut and placed in a vase has not been evaluated since the variety is primarily intended for growing in the garden.

Development:

*Vegetation.*—Very strong.

*Blooming.*—Very abundant and nearly continuous.

*Resistance to diseases.*—Excellent with respect to Blackspot and Powdery Mildew.

I claim:

1. A new and distinct variety of rose plant characterized by the following combination of characteristics:

(a) exhibits a climbing growth habit;

(b) abundantly forms attractive very double dark red blossoms having a strong fragrance that are of the old rose type, (c) forms very dense medium green semi-glossy foliage that contrasts well with the blossom coloration, (d) displays good vigor, (e) displays exceptional disease resistance, and (f) is particularly well suited for growing as attractive ornamentation in the landscape;

substantially as herein shown and described.

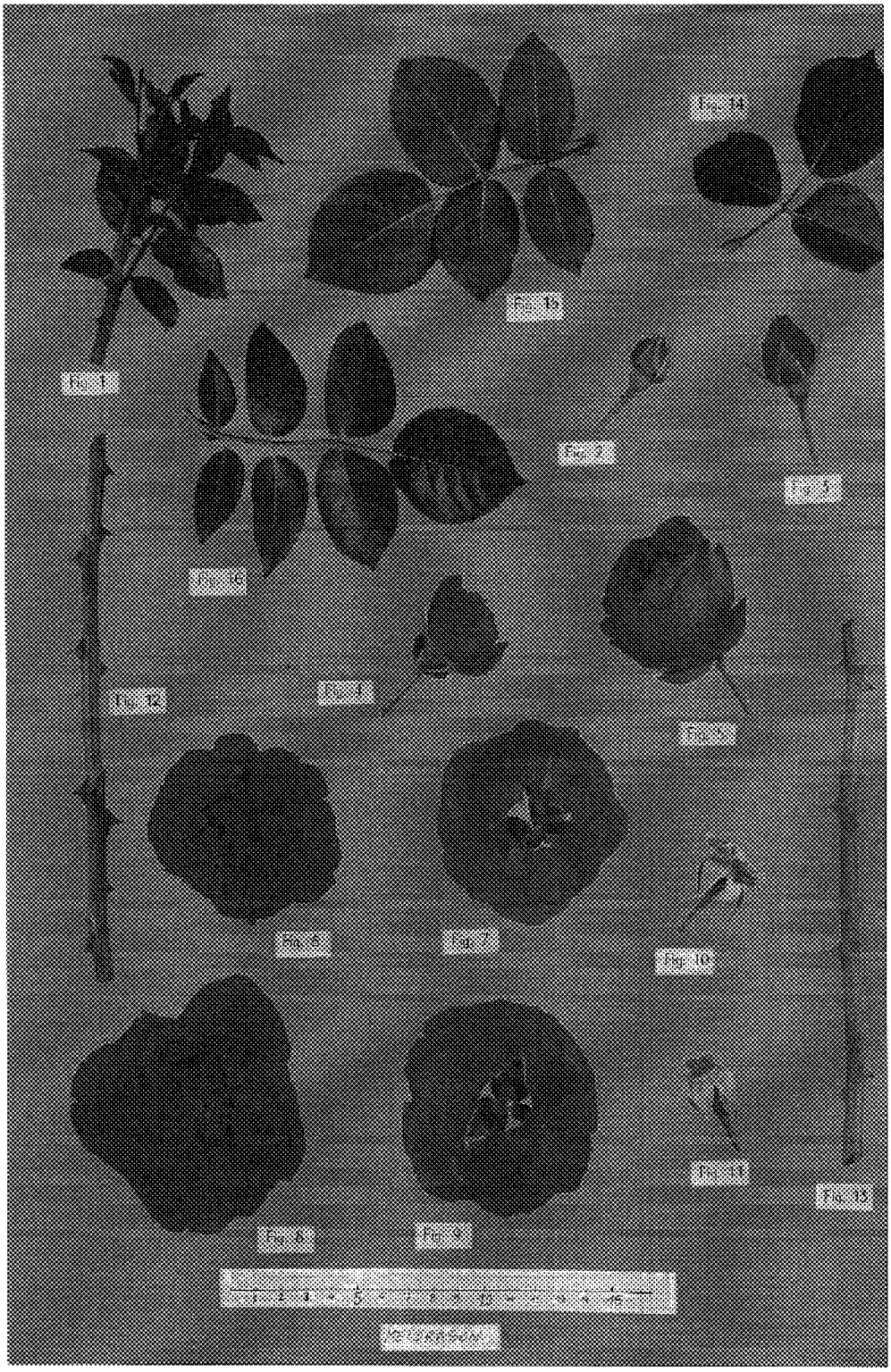

* * * * *